(12) United States Patent
Van Dyke

(10) Patent No.: US 8,021,830 B2
(45) Date of Patent: Sep. 20, 2011

(54) METHOD FOR INCREASING PLASMA VOLUME BY ADMINISTERING A PLASMA EXPANDER COMPRISING BASIC ALPHA KERATOSE

(75) Inventor: Mark E. Van Dyke, Winston Salem, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 575 days.

(21) Appl. No.: 12/209,773

(22) Filed: Sep. 12, 2008

(65) Prior Publication Data
US 2009/0017001 A1 Jan. 15, 2009

Related U.S. Application Data

(62) Division of application No. 11/205,800, filed on Aug. 17, 2005, now Pat. No. 7,439,012.

(60) Provisional application No. 60/602,207, filed on Aug. 17, 2004.

(51) Int. Cl.
*A01N 1/00* (2006.01)
*A61K 35/24* (2006.01)

(52) U.S. Cl. .......................... 435/1.1; 424/543

(58) Field of Classification Search .................. None
See application file for complete search history.

(56) References Cited

U.S. PATENT DOCUMENTS

| | | | |
|---|---|---|---|
| 3,914,802 A | 10/1975 | Reick | |
| 4,570,629 A | 2/1986 | Widra | |
| 5,932,552 A | 8/1999 | Blanchard et al. | |
| 5,948,432 A | 9/1999 | Timmons et al. | |
| 6,110,487 A | 8/2000 | Timmons et al. | |
| 6,124,265 A | 9/2000 | Timmons et al. | |
| 6,159,495 A | 12/2000 | Timmons et al. | |
| 6,159,496 A | 12/2000 | Blanchard et al. | |
| 6,270,791 B1 | 8/2001 | Van Dyke et al. | |
| 6,270,793 B1 | 8/2001 | Van Dyke et al. | |
| 6,274,155 B1 | 8/2001 | Van Dyke et al. | |
| 6,316,598 B1 | 11/2001 | Van Dyke et al. | |
| 6,371,984 B1 | 4/2002 | Van Dyke et al. | |
| 6,379,690 B2 | 4/2002 | Blanchard et al. | |
| 6,410,218 B2 | 6/2002 | Segall et al. | |
| 6,432,435 B1 | 8/2002 | Timmons et al. | |
| 6,461,628 B1 | 10/2002 | Blanchard et al. | |
| 6,506,549 B1 | 1/2003 | Segall et al. | |
| 6,544,548 B1 | 4/2003 | Siller-Jackson et al. | |
| 6,649,740 B1 | 11/2003 | Smith et al. | |
| 6,746,836 B1 | 6/2004 | Widra et al. | |
| 6,849,092 B2 | 2/2005 | Van Dyke et al. | |
| 6,914,126 B2 | 7/2005 | Van Dyke | |
| 6,989,437 B2 | 1/2006 | Van Dyke | |
| 2003/0224052 A1 | 12/2003 | Van Dyke et al. | |
| 2004/0082717 A1 | 4/2004 | Van Dyke et al. | |
| 2005/0058686 A1 | 3/2005 | Van Dyke et al. | |
| 2007/0166348 A1 | 7/2007 | Van Dyke | |

FOREIGN PATENT DOCUMENTS

EP 0 454 600 A1 4/1991
WO WO 2007/098053 8/2007

OTHER PUBLICATIONS

Schott et al., "Blood substitution and complement activation," Acta Anaesthesiologica Scandinavica 31 (7) : 559-66 (1987), abstract.
Selivanov et al., "Production of transfusion media on the base of erythrocytes and plasma substitute solutions," Gematologiia i transfuziologiia 35 (5) : 23-5 (1990), abstract.
U.S. Appl. No. 11/549,748, filed Oct. 16, 2006, Van Dyke.
Lee SJ et al. Tissue Engineering Scaffolds From Self-assembled Human Hair Keratins (2005) Polymer Preprints 46(1):112.
O'Donnell IJ et al. Studies on Oxidized Wool IV. Fractionation of Proteins Extracted from Wool on DEAE-cellulose Using Buffers Containing 8M Urea (1961) Aust J Biol Sci 14:461-474.
U.S. Appl. No. 11/673,212, filed Feb. 9, 2007, Van Dyke.
U.S. Appl. No. 11/676,072, filed Feb. 16, 2007, Van Dyke.
Crewther WG et al., The Chemistry of Keratins. Anfinsen CB Jr et al., editors. Advances in Protein Chemistry 1965. Academic Press. New York:191-346.
Goddard et al., A Study on Keratin. J. Biol. Chem. 106:605-14 (1934).
Thompson et al., Studies on Reduced Wool. *Aust. J. Biol. Sci*. 15:757-68 (1962).
Yamauchi, The development of Keratin: Characteristics of Polymer Films. Fragrance J. 21(5):62-67 (1993). (English Translation of Entire Document).
International Search Report; Written Opinion, PCT/US05/29138, Apr. 17, 2007.

*Primary Examiner* — Sandra Saucier
(74) *Attorney, Agent, or Firm* — Myers Bigel Sibley & Sajovec, P.A.

(57) ABSTRACT

A liquid plasma expander or resuscitation fluid composition for use in a subject in need thereof, comprising, consisting of; or consisting essentially of: (a) a keratin derivative (preferably alpha keratose, gamma keratose, or combinations thereof, and with basic alpha keratose preferred over acidic alpha keratose); and (b) an electrolyte solution, with the keratin derivative solubilized in the electrolyte solution to form a homogeneous liquid composition. Blood substitutes formed therefrom and methods of making and using the same are also described.

14 Claims, 8 Drawing Sheets

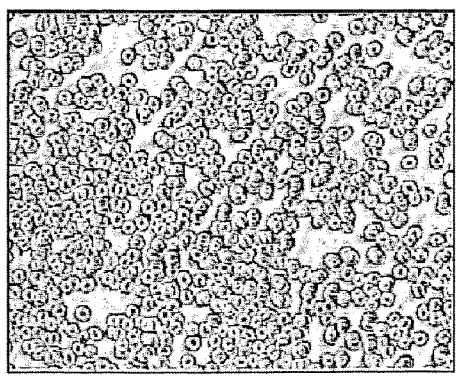
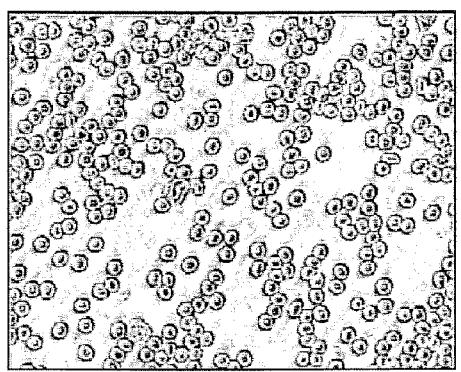
FIG. 7A  FIG. 7B
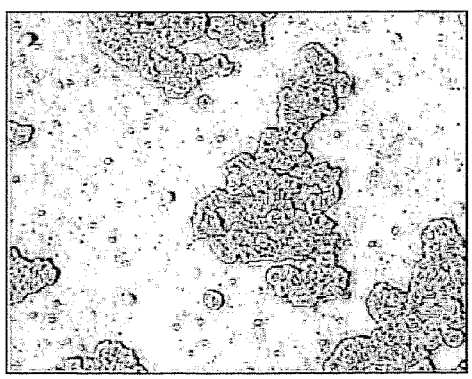
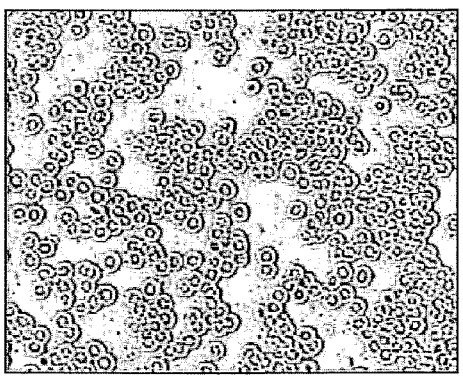
FIG. 8A  FIG. 8B

METHOD FOR INCREASING PLASMA VOLUME BY ADMINISTERING A PLASMA EXPANDER COMPRISING BASIC ALPHA KERATOSE

RELATED APPLICATIONS

This application claims priority to and is a divisional of U.S. patent application Ser. No. 11/205,800, filed Aug. 17, 2005 now U.S. Pat. No. 7,439,012, and also claims the benefit of U.S. provisional patent application Ser. No. 60/602,207, filed Aug. 17, 2004, the disclosure of each of which is incorporated by reference herein in its entirety.

GOVERNMENT FUNDING

This invention was made with Government support under contract number W81XWH-04-1-0105 from the United States Army. The US Government has certain rights to this invention.

FIELD OF THE INVENTION

The present invention is generally related to plasma expanders and blood substitutes, and is particularly related to high viscosity plasma expanders and blood substitutes.

BACKGROUND OF THE INVENTION

Many biocompatible polymeric materials have been investigated as potential plasma expanders and/or blood substitutes. Historically, there have been two approaches: 1) the use of synthetic compounds that are biocompatible, and 2) the use of biological materials that are polymeric. In the first category, materials such as hydroxyethyl starch and perfluorocarbon liquid have been evaluated (See, e.g., S. Kasper et al., *J. Clin. Anesth.* 13, 486-90 (2001); T. Kaneki et al., *Resuscitation* 52, 101-08 (2002); R. Spence et al., *Art Cells, Blood Sibst., Immobil Biotech.* 22, 955-63 (1999)). In the second group is gelatin, albumin, and crosslinlked hemoglobin (I. Tigchelaar et al., *Eur. J. Cardo-thor. Surg.* 11, 626-32 (1997); S. Gould et al., *World J. Surg.* 20, 1200-7 (1996). More recently, alpha-keratose has been suggested. See A. Widra, U.S. Pat. No. 6,746,836 (Jun. 8, 2004).

Because the functional consequences of changing the flow properties of blood are not readily predictable, the development of plasma expanders and/or blood substitutes is a complicated matter. In arterial blood vessels (diameter >100 micron) blood viscosity is proportional to hematocrit (Hct) squared, and in the smaller vessels it is linearly proportional to Hct. In the systemic circulation, Hct is approximately constant down to 100 micron diameter vessels. It falls monotonically down to the capillaries where it is approximately half of the systemic value. The reverse occurs in the venous circulation, where it is higher than arterial because of fluid filtration in the microcirculation.

In acute conditions such as accompanying severe trauma, the decrease of Hct is not deemed dangerous until the transfusion trigger (blood hemoglobin content beyond which a blood transfusion is indicated) is reached. However, this exposes the vasculature to low blood viscosity when conventional plasma expanders are used to maintain blood volume. There appears to be no well-defined benefit to lowering blood viscosity, excepting when it is pathologically high, and lowering blood viscosity through hemodilution is considered to have no adverse effects. Richardson and Guyton determined that changes in blood viscosity are accompanied by compensatory changes in cardiac output, which compensate for changes in intrinsic oxygen carrying capacity of blood due to changes in Hct (T. Richardson et al., *Am. J. Physiol.* 197, 1167-70 (1959)). This was confirmed systemically and in the microcirculation (K. Messmer, *Surg. Clins. N. Am.* 55, 659-78 (1975); S. Mirhashemi et al., *Am. J. Physiol* 254 (*Heart Circ. Physiol.* 13) H411-16 (1988); A. Tsai et al., *Int. J. Microcirc: Clin. Exp* 10, 317-34 (1991)). Empirically, the transfusion trigger is set at 7 g Hb/dl (Hct~22%).

Microvascular Hcts are lower than systemic due to the presence of a plasma layer that proportionally occupies a greater portion of the vessel lumen, thus blood viscosity is also lower. The transition from macro to microcirculation in terms of vessel dimensions, Hct, and hemodynamics is gradual. Blood theological properties also change gradually and blood viscosity in the circulation depends on location. The reduction of Hct with a crystalloid or colloidal plasma expander tends to equalize the theological properties of blood and viscosity throughout the circulation.

When a plasma expander is used to remedy hemorrhage, systemic Hct decreases, significantly reducing blood viscosity in large vessels due to the squared dependence of viscosity on Hct. Viscosity of blood in small vessels is much less affected since Hct is low to begin with. Conversely, small vessel blood viscosity is greatly influenced by the viscosity of the plasma expander. If its viscosity is low, blood viscosity drops significantly in the small vessels as well as in the large vessels, although for somewhat different reasons. In conventional theory, this reduction in viscosity increases blood flow and may improve oxygen delivery.

However, the literature supports the concept that high viscosity plasma is either beneficial, or has no adverse effect in conditions of extreme hemodilution. Waschke et al. found that cerebral perfusion is not changed when blood is replaced with fluids of the same intrinsic oxygen carrying capacity over a range of viscosities varying from 1.4 cp to 7.7 cp (K. Waschke et al., *J. Cereb. Blood Flow & Metab.* 14, 871-976 (1994)) Krieter et al., varied the viscosity of plasma by adding dextran 500 k Daltons (Da) and found that medians in tissue $pO_2$ in skeletal muscle where maximal at a plasma viscosity of 3 cp, while for liver the maximum occurred at 2 cp (H. Krieter et al., *Acta Anaest. Scad.* 39, 326-44 (1995)). In general they found that up to a 3 fold increase in blood plasma viscosity had no effect on tissue oxygenation and organ perfusion when blood was hemodiluted. de Witt et al., found elevation of plasma viscosity causes sustained NO-mediated dilatation in the hamster muscle microcirculation (C. deWitt et al., *Pflugers Arch.* 434, 54-61 (1997)).

Hct reductions should improve blood perfusion through the increase of blood fluidity. However at a Hct near to and beyond the transfusion trigger the heart cannot further increase flow and as viscosity falls, so does blood pressure. The fall of pressure is deleterious for tissue perfusion because it decreases functional capillary density (FCD) in the normal circulation and in hypotension following hemorrhage (L. Lindbom et al., *Int. J. Microcirc: Clin. Exp* 4, 121-7 (1985)). FCD is a critical microvascular parameter in survival during acute blood losses. In a hamster model subjected to 4-hr 40 mmHg hemorrhagic shock, the fall of FCD accurately predicts outcome and separates survivors from non survivors when this parameter decreases below 40% of control (H. Kerger et al., *Am. J. Physiol* 270 (*Heart. Circ. Physiol.* 39), H827-36 (1996)).

High viscosity plasma restores mean arterial pressure (MAP) in hypotension without vasoconstriction. Furthermore, the shift of pressure and pressure gradients from the systemic to the peripheral circulation increases blood flow, which in combination with increased plasma viscosity maintains shear stress in the microcirculation. This is needed for shear stress dependant NO and prostaglandin release from the endothelium and to maintain FCD (J. Frangos et al., *Science* 227, 1477-79 (1985)). Conversely, reduced blood viscosity decreases shear stress and the release of vasodilators, causing vasoconstriction and offsetting any benefit of reducing the theological component of vascular resistance. Since resistance depends on the $4^{th}$ power of vascular radius and the $1^{st}$ power of blood viscosity, the effect of reducing blood viscosity with a low viscosity plasma expander is that it reduces oxygen delivery to the tissue once blood viscosity falls below a threshold value. This threshold has been determined in our experimental model as about 2.5 cp.

Tissue perfusion with reduced blood viscosity may be deleterious at the cellular/endothelial level. There is evidence that genes are activated following changes in the mechanical environment of cells. It is also been established that the endothelium uniquely responds to changes in its mechanical and oxygen environment according to programmed genetic schemes. Among these responses is the mechanism for apoptosis (cell self destruction), which is activated through a genetically controlled suicide process that eliminates cells no longer needed or excessively damaged. In this context, hemodilution with low viscosity plasma expanders may cause cellular and tissue damage due to hypoxia and/or to the reduced vessel wall shear stress. Hypoxia/ischemia may contribute to endothelial impairment due to inflammatory reactions. Activation of endothelium, platelets and neutrophils, leading to additional damage through the liberation of cytokines, can induce endothelial apoptosis (B. Robaye et al., *Am. J. Pathol.* 38, 447-53 (1991)).

Studies in a hamster model show that extreme hemodilution (where Hct is 20% of control) with dextran 70 kDa, causes hypotension and a drop in FCD to near pathological values (A. Tsai et al., *Proc. Natl. Acacd. Sci. USA* 95, 6590-5 (1998); A. Tsai. Transfusion 41, 1290-8 (2001)). This is prevented by increasing plasma viscosity so that the diluted blood has a systemic viscosity of about 2.8 cp, which was achieved by infusing dextran 500 kDa. Thus, high viscosity plasma substitutes can be an alternative to the use of blood for maintaining MAP and an adequate level of FCD (A. Tsai et al., *Biorheology* 38, 229-37 (2001)). However, the known high viscosity plasma expanders such as gelatin, albumin, hydroxyethyl starch, polyvinyl-pyrrolidine, and dextran are all either non-human derived or synthetic. As such, each suffers from considerable limitations in their clinical applicability due to biocompatibility, cost, or both. What is needed is a fluid based on a substantially biocompatible material that is inexpensive, pathogen free and ambient storable. Resuscitation fluids based on keratins offer this potential.

Human hair is one of the few autologous tissues that can be obtained without additional surgery. It is also a rich source of keratins. Equally important, the biocompatibility of keratins within a species, and indeed across species is high, making allogenous and xenogenous keratins viable candidates for medical applications. The keratins found in hair, wool, and other keratinous tissues can be extracted and purified using methods known in the art, and used for formulating plasma substitutes with fluid properties that will maintain MAP and FCD. Depending on the species from whence the keratins come, the biocompatibility can also be optimized with human hair keratins being the most optimal. Keratin fluids are inexpensive to produce, can be sterilized, and are stable under ambient temperature storage.

However, the keratin-based fluid described in A. Widra would not appear to be the most optimized resuscitation medium based on the new paradigm of preserving FCD for three important reasons. First, the type of keratin used in the experiments was a highly hydrolyzed form of keratose, represented in Scheme 1 below, which is not likely to be capable of attaining the viscosic properties required by the application.

Scheme 1. A representation of the keratose analog of keratin.

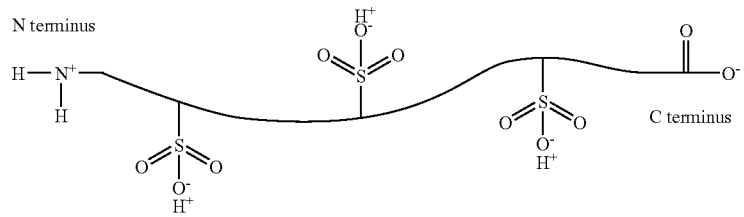

Second, hydrolyzed forms of keratose are compatible with blood in that they do not instigate appreciable levels of red blood cell aggregation, but their oncotic pressure is too low to be of benefit. Third, less hydrolyzed, high molecular weight forms of keratose tend to aggregate red blood cells, thus making the material deleterious to the restoration of FCD. Hence their remains a need for new approaches to developing keratin-based high viscosity plasma substitutes.

SUMMARY OF THE INVENTION

A first aspect of the invention is a liquid plasma expander or resuscitation fluid composition for use in a subject in need thereof, comprising, consisting of, or consisting essentially of: (a) a keratin derivative (preferably alpha keratose, gamma keratose, or combinations thereof); and (b) an electrolyte solution, with the keratin derivative solubilized in the electrolyte solution to form a homogeneous liquid composition.

A particular aspect of the foregoing is a liquid plasma expander composition in which the keratin derivative comprises alpha keratose, where the alpha keratose consists of at least 80, 90, 95 or 99 percent by weight of basic alpha keratose (or more), and where the alpha keratose consists of not more than 20, 10, 5 or 1 percent by weight of acidic alpha keratose (or less).

A particular aspect of the foregoing is a liquid plasma expander composition for use in a subject in need thereof, comprising, consisting of or consisting essentially of: (a) from 0.1 to 10 or 20 percent by weight of basic alpha keratose; (b) from 0 to 5 or 10 percent by weight of gamma keratose; and (c) from 80 or 90 to 99.9 percent by weight of an electrolyte solution. Preferably, the basic alpha keratose and the gamma keratose are solubilized in said electrolyte solution to form a homogeneous liquid composition. Preferably the homogeneous liquid composition has a pH of 7 to 8 or 9; preferably the homogeneous liquid composition has an osmolarity of 100 or 200 to 500 or 600 milliosmoles/Liter; and preferably the homogeneous liquid composition has a viscosity of 2 or 4 to 15 or 20 centipoise. Preferably the homogeneous liquid composition, when contacted to red blood cells, forms aggregates of said blood cells of less than 25 microns in diameter.

The basic alpha keratose is preferably produced by separating basic alpha keratose from a mixture of acidic and basic alpha keratose, e.g., by ion exchange chromatography, and preferably the basic alpha keratose has an average molecular weight of from 10 to 100 or 200 kilodaltons. Optionally but preferably the process further comprises the steps of re-dissolving said basic alpha-keratose in a denaturing solution (such as a buffer solution), optionally in the presence of a chelating agent to complex trace metals, and the re-precipitating the basic alpha keratose from the denaturing solution. It will be appreciated that the composition preferably contains not more than 5, 2, 1, or 0.1 percent by weight of acidic alpha keratose, or less.

A second aspect of the present invention is a blood substitute composition for use in a subject in need thereof, comprising, consisting of, or consisting essentially of: a plasma expander or resuscitation fluid as described above, and red blood cells (RBCs) where the RBCs form an essentially single cell suspension of RBCs therein.

A third aspect of the present invention is a method of increasing plasma volume in a subject in need thereof, comprising administering the subject a plasma expander or resuscitation fluid composition as described above in an amount effective to increase the plasma volume of said subject.

A fourth aspect of the present invention is a method of increasing the volume of available blood substitute for treatment in a subject in need thereof, comprising the steps of: (a) obtaining a volume of donor blood and determining the Hct; (b) separating and isolating the RBCs from said donated blood; and (c) diluting said isolated RBCs to a final Hct of not less than 10% of the original Hct but not greater than 70% by adding an appropriate amount of the plasma expander composition as described above.

A further aspect of the present invention is the use of a keratin derivative as described herein for the preparation of a plasma expander or resuscitation fluid for carrying out a method as described herein.

BRIEF DESCRIPTION OF THE DRAWINGS

FIG. 2a shows whole blood aggregation with 1 mg/mL Collagen.

FIG. 2b shows whole blood aggregation with 2% alpha-keratose.

FIG. 2c shows whole blood aggregation with 2% gamma keratose.

FIG. 2d shows whole blood aggregation with 2% alpha-kerateine.

FIG. 7. Lightly citrated samples of 4% γ-keratose (a) and α-keratose (b) in Ringer's lactate mixed 1:1 with whole blood. These initial keratose fluids were of low viscosity and consequently did not instigate RBC aggregation or platelet activation. SDS-PAGE analysis confirmed that the proteins were excessively hydrolyzed which may have contributed to their apparent blood compatibility.

FIG. 8. Fluids prepared in PBS at pH 7.4 with 5 weight % acidic (a) and basic (b) α-keratose were mixed 1:1 with whole blood. RBC aggregation is evident in the acidic fluid as positively charged keratin proteins interact with the blood cells. The negatively charged basic keratins repel the negatively charged blood cells and prevent aggregation.

DETAILED DESCRIPTION OF THE PREFERRED EMBODIMENTS

Figure 1:
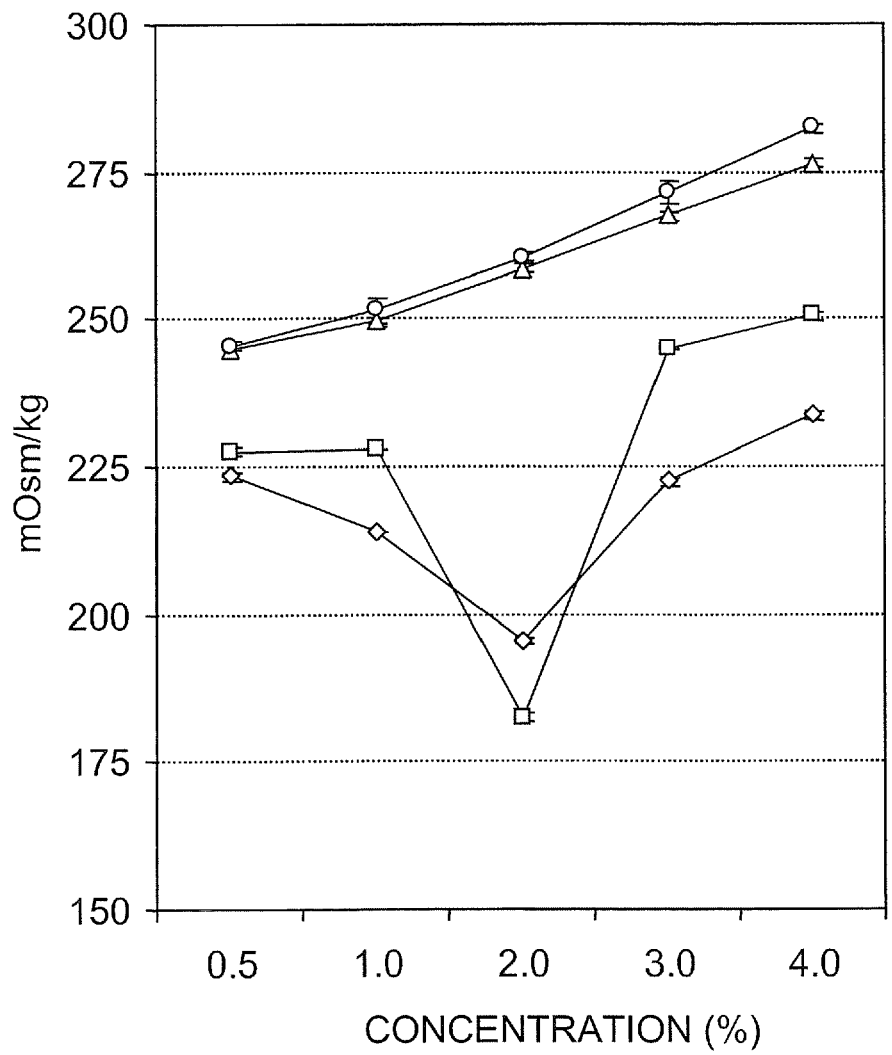
FIG. 1 shows the osmolarity of various keratin resuscitation fluids. Diamonds represent alpha-keratose fluids; squares represent gamma keratose fluids; triangles represent alpha-kerateine fluids; circles represent gamma-kerateine fluids.
Figure 2A:
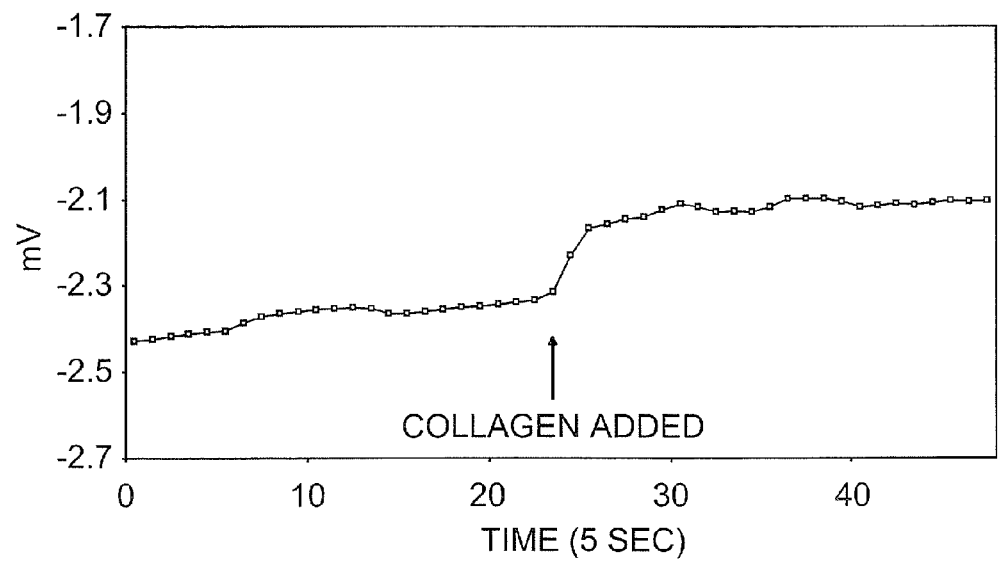
FIG. 2a-d shows the thrombogenic potential of keratin resuscitation fluids as evaluated by whole blood aggregometry.
Figure 2B:
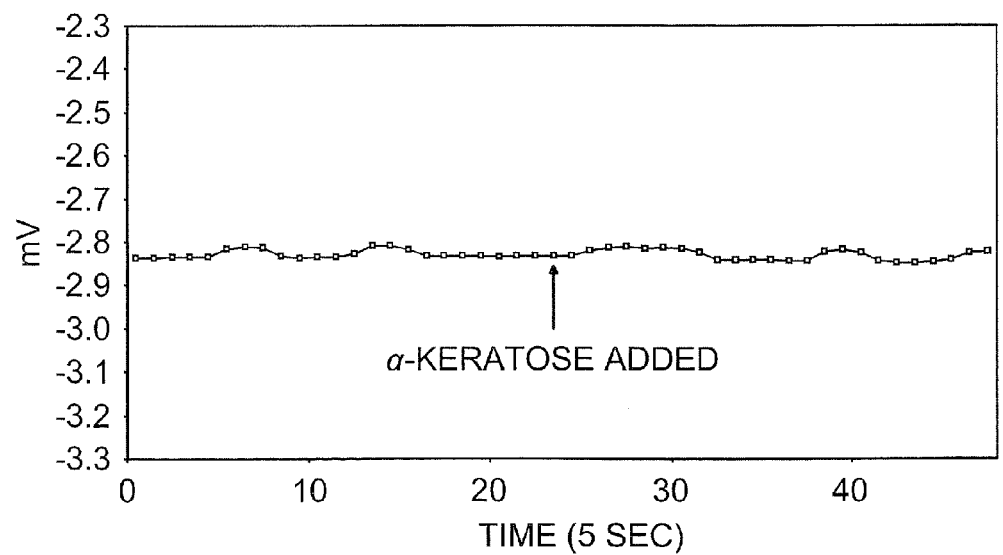
Figure 2C:
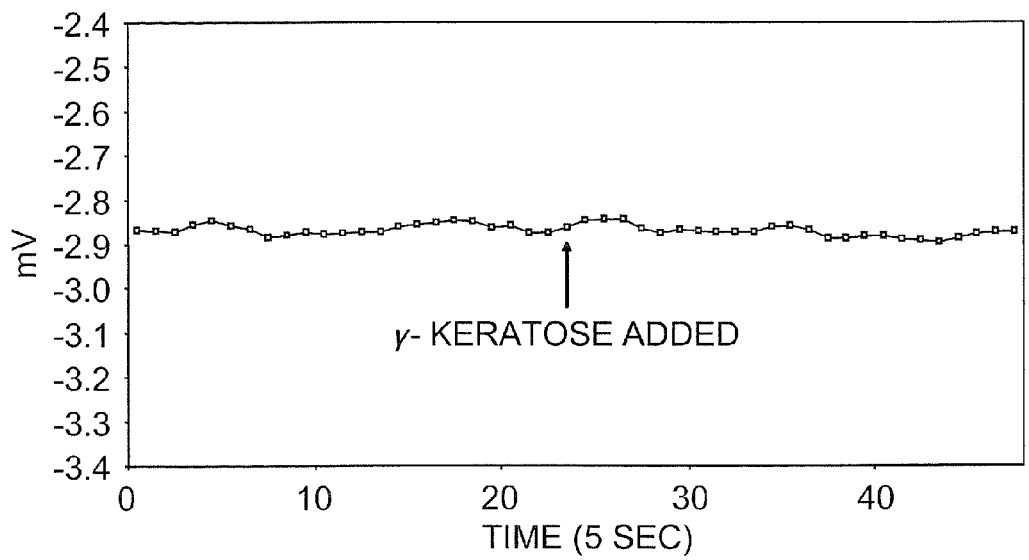
Figure 2D:
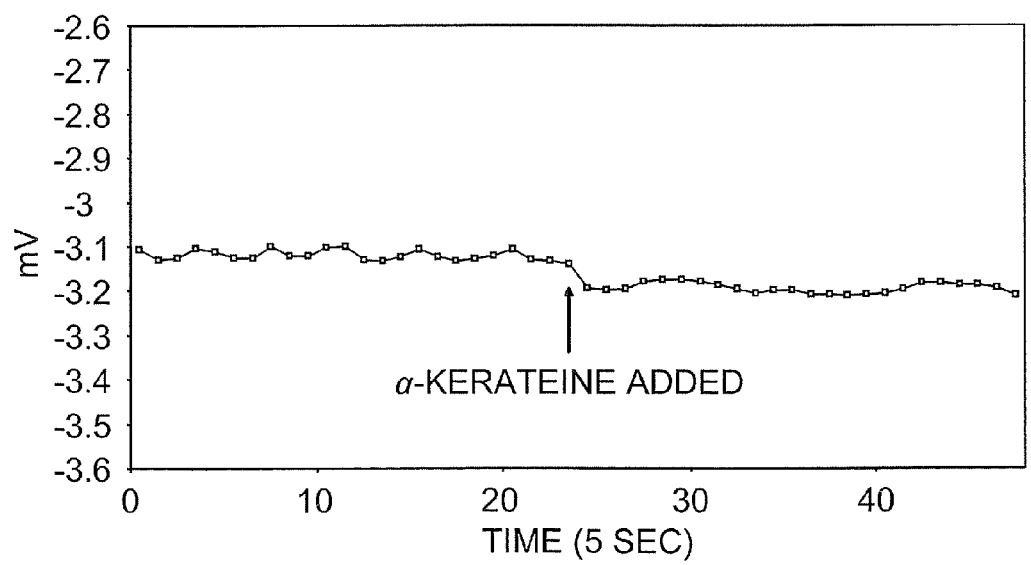

"Solubilized" as used herein refers to a compound that is carried by a solvent to form a homogeneous mixture therewith, without precipitation or separation of that compound from the solvent. Examples of such homogeneous mixtures include solutions, suspensions, dispersions, and microemulsions. Preferably the homogeneous mixtures do not scatter visible light (i.e., are "clear" on visual inspection).

"Dissolved" as used herein refers to a compound or solute carried by another liquid or solvent in the form of a single-phase solution.

"Subjects" (or "patients") to be treated with the methods and compositions described herein include both human subjects and animal subjects (particularly other mammalian subjects such as dogs, cats, horses, monkeys, etc.) for veterinary purposes. Human subjects are particularly preferred. The subjects may be male or female and may be any age, including neonate, infant, juvenile, adolescent, adult, and geriatric subjects.

"Plasma expander" as used herein refers to a composition that may be used to increase the volume of blood plasma in a subject in need thereof. The plasma expander itself may be blood-free. In some embodiments the plasma expander may serve as a resuscitation fluid.

"Resuscitation fluid" as used herein refers to a plasma expander that further serves to maintain, pretent further decrease, and/or prevent accelerated decrease of functional capillary density (FCD) in a subject. Plasma expanders of the present invention are preferably also resuscitation fluids.

"Keratin derivative" as used herein refers to any keratin derivative or mixture thereof, including but not limited to alpha keratose, gamma keratose, alpha kerateine, gamma kerateine, meta-keratin, keratin intermediate filaments, and combinations thereof.

"Electrolyte solution" as used herein includes saline solution, mixed salt or buffer solutions such as Ringers solution, Lactated Ringers solution, and combinations thereof.

"Blood substitute" as used herein refers to any fluid capable of replicating the biochemical (e.g. oxygen carrying) and biomechanical (e.g. viscosic) capabilities of whole blood.

The disclosures of all United States patents cited herein are to be incorporated by reference herein in their entirety.

1. Keratin materials. Keratin materials are derived from any suitable source including but not limited to wool and human hair. In one embodiment keratin is derived from end-cut human hair, obtained from barbershops and salons. The material is washed in hot water and mild detergent, dried, and extracted with a nonpolar organic solvent (typically hexane or ether) to remove residual oil prior to use.

Scheme 2. General representations of (a) oxidation and (b) reduction of disulfide crosslinks in keratin. These reactions cleave the sulfur-sulfur bond in cystine residues, thereby destroying the superstructure and rendering the keratins soluble in the reaction media.

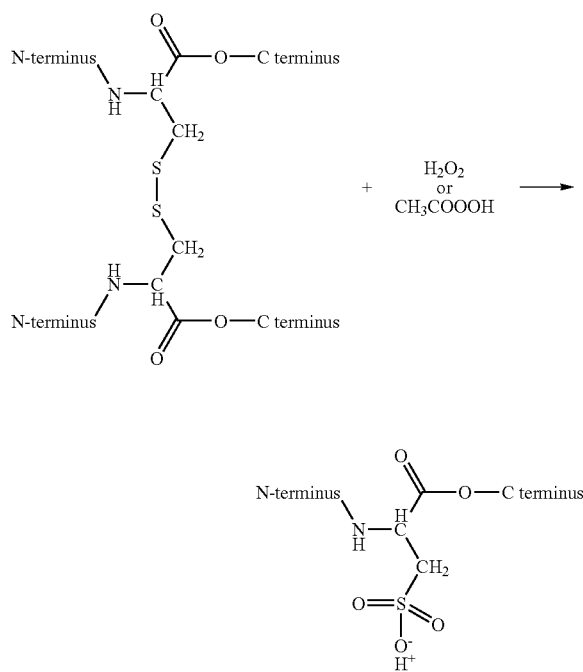

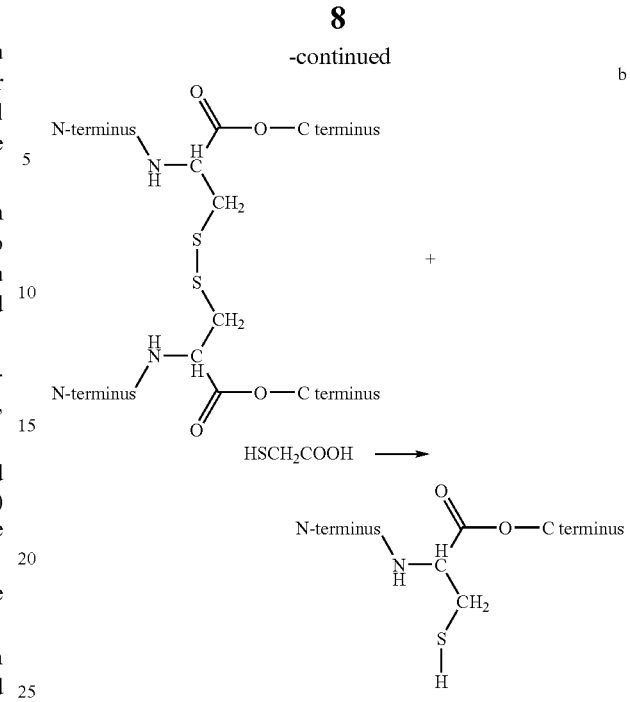

Keratose Fractions. Keratose fractions are obtained by any suitable technique. In one embodiment they are obtained using the method of Alexander and coworkers (P. Alexander et al., *Biochem. J.* 46, 27-32 (1950)). Basically, the hair is reacted with an aqueous solution of peracetic acid at concentrations of less than ten percent at room temperature for 24 hours. The solution is filtered and the alpha-keratose fraction precipitated by addition of mineral acid to a pH of ca. 4. The alpha-keratose is separated by filtration, washed with additional acid, followed by dehydration with alcohol, and then dried under vacuum. Increased purity can be achieved by redissolving the keratose in a denaturing solution such as 7M urea, aqueous ammonium hydroxide solution, or 20 mM tris base buffer solution, re-precipitating, re-dissolving, dialyzing against deionized water, and re-precipitating at pH 4.

The gamma-keratose fraction remains in solution at pH 4 and is isolated by addition to a water-miscible organic solvent such as alcohol, followed by filtration, dehydrated with additional alcohol, and dried under vacuum. Increased purity can be achieved by redissolving the keratose in a denaturing solution such as 7M urea, aqueous ammonium hydroxide solution, or 20 mM tris buffer solution, reducing the pH to 4 by addition of a mineral acid, removing any solids that form, neutralizing the supernatant, re-precipitating the protein with alcohol, re-dissolving, dialyzing against deionized water, and reprecipitating by addition to alcohol. The amount of alcohol consumed in these steps can be minimized by first concentrating the keratose solution by distillation.

Kerateine Fractions. Kerateine fractions are obtained using a combination of the methods of Bradbury and Chapman (J. Bradbury et al., *Aust. J. Biol. Sci.* 17, 960-72 (1964)) and Goddard and Michaelis (D. Goddard et al., *J. Biol. Chem.* 106, 605-14 (1934)). Essentially, the cuticle of the hair fibers is removed ultrasonically in order to avoid excessive hydrolysis and allow efficient reduction of cortical disulfide bonds in a second step. The hair is placed in a solution of dichloroacetic acid and subjected to treatment with an ultrasonic probe. Further refinements of this method indicate that conditions using 80% dichloroacetic acid, solid to liquid of 1:16, and an ultrasonic power of 180 Watts are optimal (H. Ando et al.,

*Sen'i Gakkaishi* 31(3), T81-85 (1975)). Solid fragments are removed from solution by filtration, rinsed and air dried, followed by sieving to isolate the hair fibers from removed cuticle cells.

Following ultrasonic removal of the cuticle, alpha- and gamma-kerateines are obtained by reaction of the denuded fibers with mercaptoethanol. Specifically, a low hydrolysis method will be used at acidic pH (E. Thompson et al., *Aust. J. Biol. Sci.* 15, 757-68 (1962)). In a typical reaction, hair is extracted for 24 hours with 4M mercaptoethanol that has been adjusted to pH 5 by additional of a small amount of potassium hydroxide in deoxygenated water containing 0.02M acetate buffer and 0.001M surfactant.

The solution is filtered and the alpha-kerateine fraction precipitated by addition of mineral acid to a pH of ca. 4. The alpha-kerateine is separated by filtration, washed with additional acid, followed by dehydration with alcohol, and then dried under vacuum. Increased purity is achieved by re-dissolving the kerateine in a denaturing solution such as 7M urea, aqueous ammonium hydroxide solution, or 20 mM tris buffer solution, re-precipitating, re-dissolving, dialyzing against deionized water, and re-precipitating at pH 4.

The gamma-kerateine fraction remains in solution at pH 4 and is isolated by addition to a water-miscible organic solvent such as alcohol, followed by filtration, dehydrated with additional alcohol, and dried under vacuum. Increased purity is achieved by redissolving the kerateine in a denaturing solution such as 7M urea, aqueous ammonium hydroxide solution, or 20 mM tris buffer solution, reducing the pH to 4 by addition of a mineral acid, removing any solids that form, neutralizing the supernatant, re-precipitating the protein with alcohol, re-dissolving, dialyzing against deionized water, and reprecipitating by addition to alcohol. The amount of alcohol consumed in these steps can be minimized by first concentrating the keratose solution by distillation.

In an alternate method, the kerateine fractions are obtained by reacting the hair with an aqueous solution of sodium thioglycolate.

Meta-Keratins. Meta-keratins are synthesized from both the alpha- and gamma-fractions of kerateine using substantially the same procedures. Basically, the kerateine is dissolved in a denaturing solution such as 7M urea, aqueous ammonium hydroxide solution, or 20 mM tris buffer solution. Pure oxygen is bubbled through the solution to initiate oxidative coupling reactions of cysteine groups. The progress of the reaction is monitored by an increase in molecular weight as measured using SDS-PAGE. Oxygen is continually bubbled through the reaction solution until a doubling or tripling of molecular weight is achieved. The pH of the denaturing solution can be adjusted to neutrality to avoid hydrolysis of the proteins by addition of mineral acid.

Keratin Intermediate Filaments. IFs of human hair fibers are obtained using the method of Thomas and coworkers (H. Thomas et al., *Int. J. Biol. Macromol.* 8, 258-64 (1986)). This is essentially a chemical etching method that reacts away the keratin matrix that serves to "glue" the IFs in place, thereby leaving the IFs behind. In a typical extraction process, swelling of the cuticle and sulfitolysis of matrix proteins is achieved using 0.2M $Na_2SO_3$, 0.1M $Na_2O_6S_4$ in 8M urea and 0.1M Tris-HCl buffer at pH 9. The extraction proceeds at room temperature for 24 hours. After concentrating, the dissolved matrix keratins and IFs are precipitated by addition of zinc acetate solution to a pH of ca. 6. The IFs are then separated from the matrix keratins by dialysis against 0.05M tetraborate solution. Increased purity is obtained by precipitating the dialyzed solution with zinc acetate, redissolving the IFs in sodium citrate, dialyzing against distilled water, and then freeze drying the sample.

2. Formulations. Dry powders may be formed of keratin derivatives as described above in accordance with known techniques such as freeze drying or lyophilization. In some embodiments, a liquid plasma expander composition of the invention may be produced by mixing such a dry powder composition form with an aqueous solution to produce a homogeneous liquid plasma expander composition comprising an electrolyte solution having said keratin derivative solubilized therein. The mixing step can be carried out at any suitable temperature, typically room temperature, and can be carried out by any suitable technique such as stirring, shaking, agitation, etc. The salts and other constituent ingredients of the electrolyte solution (e.g., all ingredients except the keratin derivative and the water) may be contained entirely in the dry powder, entirely within the aqueous composition, or may be distributed between the dry powder and the aqueous composition. For example, in some embodiments, at least a portion of the constituents of the electrolyte solution are contained in the dry powder.

In the composition the keratin derivatives (particularly alpha and/or gamma kerateine and alpha and/or gamma keratoses) have an average molecular weight of from about 10 to 70 or 100 kiloDaltons. Other keratin derivatives, particularly meta-keratins, may have higher average molecular weights, e.g., up to 200 or 300 kiloDaltons. In general, the keratin derivative (this term including combinations of derivatives) may be included in the composition in an amount of from about 0.1, 0.5 or 1 percent by weight up to 3, 4, 5, or 10 percent by weight. The composition when mixed preferably has a viscosity of about 1 or 1.5 to 4, 8, 10 or 20 centipoise. Viscosity at any concentration can be modulated by changing the ratio of alpha to gamma keratose. Studies have shown that viscosities as high as 7.7 have no deleterious effects (see K. Waschke et al., *J. Cereb. Blood Flow & Metab.* 14, 871-976 (1994) and H. Krieter et al., *Acta Anaest. Scad.* 39, 326-44 (1995)).

The electrolyte solution may be any suitable electrolyte solution, including but not limited to saline solution (particularly normal saline), Ringer's solution, lactated Ringer's solution, commercially available solutions such as NORMO-SOL®-R isotonic fluid (available from Abbott Laboratories, Chicago, Ill. USA), and combinations thereof. Examples of suitable electrolyte compositions include but are not limited to those described in U.S. Pat. No. 6,746,836 to Widra. The complete composition when mixed preferably has an osmolarity of 200 to 400 milliosmoles/Liter and a pH of about 7 to 8.

The composition is preferably sterile and non-pryogenic. The composition may be provided preformed and aseptically packaged in a suitable container, such as a flexible polymeric bag or bottle, or may be provided as a kit of sterile dry powder in one container and sterile aqueous solution in a separate container for mixing just prior to use. When provided pre-formed and packaged in a sterile container the composition preferably has a shelf life of at least 4 or 6 months (up to 2 or 3 years or more) at room temperature, prior to substantial loss of viscosity (e.g., more than 10 or 20 percent) and/or substantial precipitation of the keratin derivative (e.g., settling detectable upon visual inspection).

3. Subjects and administration. As noted above, the present invention provides a method of increasing plasma volume in a subject (human or animal) in need thereof, or of replacing or augmenting whole blood in a subject in need thereof, comprising administering said subject a plasma expander or blood substitute, respectively, as described above in an amount effective to resuscitate said subject.

The dose or volume administered to the subject will depend upon factors such as the age and general health of the subject, the particular condition of the subject, the disorder being treated and the severity of that disorder, etc., and can be determined by skilled persons in accordance with known techniques. In some embodiments the volume administered will be between about 0.5 or 1 to 50 or 70 mL per Kg subject body weight. In some embodiments the volume administered will be from 0.1 or 0.2 Liters up to 3 or 4 Liters total per subject. For example, the resuscitation fluid can be utilized up to the transfusion trigger (Hct. of ca. 22%). This means that for an average man with a Hct of ca. 54% and a blood volume of ca. 5 L, he can be transfused with up to 3 L of plasma expander/resuscitation fluid of the invention before blood transfusion is necessary. Hct and blood volume vary by gender and age, so target volumes would vary accordingly. In another example, for neonatal shock, the composition may be administered in aliquots of between 2 to 10 mL per Kg every few minutes as necessary.

In general, subjects in need thereof include subjects in shock, typically due to acute or chronic bleeding. Particular subjects include but are not limited to subjects suffering from a laceration, incision or other injury to any portion of the body, such as an extremity, or suffering from internal injury to an organ such as the liver. The internal injury may be acute, as resulting from trauma, or chronic, such as a bleeding ulcer or diverticulitis.

Subjects that may be treated by the methods of the invention include patients undergoing a surgical procedure, where bleeding is a consequence of the surgical procedure. In cases where the surgical procedure is elective, the subject may donate whole blood before the surgery to be used in the preparation of an autologous keratin-based blood substitute.

Subjects that may be treated by the methods of the invention include burn victims, particularly severe burn victims, where blood fluid is required to carry and clear burn toxins from the body to avoid organ poisoning and organ failure.

In addition to administer to subjects, the plasma expander compositions of the present invention may be used as bath, storage or rinse compositions for organs (particularly mammalian organs of the same species as described above in connection with subjects) in connection with organ transplant procedures. Suitable organs include but are not limited to kidney, heart, lung, liver, etc.

EXAMPLE 1

Production of Keratoses 50 grams of clean dried hair are oxidized using 1,000 mL of 2 weight/volume % peracetic acid by gentle shaking at 37° C. for 12 hours. The oxidized hair is recovered by sieve and rinsed free of residual oxidant using copious amounts of deionized (DI) water. The damp hair is extracted with 2,000 mL of 0.1M tris base at 37° C. with gentle shaking for 3 hours. The hair is separated by sieve and the liquid retained. The swollen hair is further extracted with 2,000 mL of DI water at 37° C. with gentle shaking for 1 hour. The hair is separated by sieve and the liquid retained. A third and final extraction of the swollen hair is accomplished with 25000 mL of DI water at 37° C. with gentle shaking for 1 hour. The hair is separated by sieve and the liquid retained. The three extracts are combined and residual solids removed by centrifugation and filtration. The keratose solution is titrated to pH 6 by dropwise addition of acid and loaded onto a preconditioned ionic exchange column containing a weak ion exchange resin such as DEAL Sepharose™. The column is washed with an equal volume of 10 mM tris buffer at pH 6 and the eluent saved for another use. The bound keratose is removed from the column by washing with 100 mM tris buffer with 2M NaCl at pH 12. This fraction is referred to as basic keratose. The basic keratose is further separated into its gamma and alpha fractions by selective precipitation. For example, basic alpha-keratose is isolated by reducing the pH of the solution to 4.2 with dropwise addition of acid. The precipitate that forms is isolated by centrifugation and/or filtration. The subject resuscitation fluid is formulated using either pure alpha or a mixture of alpha and gamma keratoses. Regardless, the basic keratose solution is neutralized by addition of acid and dialyzed by tangential flow ultrafiltration against DI water for approximately 12 hours (nominal low molecular weight cutoff of 5 kDa). The dialyzed sample is concentrated by removal on excess water on a rotary evaporator and the basic keratose powder isolated by lyophilization. Resuscitation fluids are formulated from this powder by addition to phosphate-buffered saline at pH 7.4 and a concentration sufficient to achieve a viscosity of between 4 and 20 centipoise, preferably 8 centipoise.

EXAMPLE 2

Production of Alpha-Keratose Fraction

Alpha-keratose is isolated from the extract solution prepared in Example 1 by dropwise addition of acid until the pH of the solution reaches approximately 4.2. Preferred acids include sulfuric, hydrochloric, and acetic acid. A most preferred acid is concentrated hydrochloric acid. Precipitation of the alpha fraction begins at around pH 6.0 and continues until approximately 4.2. Fractional precipitation can be utilized to isolate different ranges of protein with different isoelectric properties. Solid alpha-keratose is recovered by centrifugation or filtration. The alpha-keratose is further purified by re-dissolving the solids in a denaturing solution. The same denaturing solutions as those utilized for extraction can be used, however a preferred denaturing solution is Trizma base (also called tris base). Ethylene diamine tetraacetic acid (EDTA) is added to complex trace metals formed in hair. A preferred denaturing solution is 20 mM tris base with 20 mM EDTA. The alpha-keratose is re-precipitated from this solution by dropwise addition of hydrochloric acid to a final pH of 4.2. Isolation of the solid is by centrifugation or filtration. This process can be repeated several times to further purify the alpha-keratose.

EXAMPLE 3

Production of Gamma-Keratose Fraction

The gamma-keratose fraction is isolated by precipitation to a water-miscible non-solvent. Suitable non-solvents include ethanol, methanol, acetone, and the like. A most preferred non-solvent is ethanol. To affect precipitation, the gamma-keratose solution can be concentrated by evaporation of excess water. After removal of the alpha-keratose, the concentration of gamma-keratose from a typical extraction solution is approximately 1-2%. This solution can be concentrated to approximately 10-20% by removal of 90% of the water. This can be done using vacuum distillation. After concentration, the gamma-keratose solution is added dropwise to an excess of cold non-solvent. A most preferred method is to concentrate the gamma-keratose solution to approximately 10% and add it dropwise to an 8-fold excess of cold ethanol.

The gamma-keratose is isolated by centrifugation or filtration and dried. Suitable methods for drying include freeze drying (lyophilization), air drying, vacuum drying, or spray drying. A most preferred method is freeze drying.

EXAMPLE 4

Production of Kerateines

A preferred method for the production of kerateines is by reduction with thioglycolic acid or beta-mercaptoethanol. A most preferred reductant is thioglycolic acid. Preferred concentrations range from 1 to 10 molar (M), the most preferred being approximately 1.0M. Those skilled in the art will recognize that slight modifications to the concentration can be made to affect varying degrees of reduction, with concomitant alterations in pH, reaction time, temperature, and liquid to solid ratio. A preferred pH is between 9 and 11. A most preferred pH is 10.2. The pH of the reduction solution is altered by addition of base. Preferred bases include transition metal hydroxides and ammonium hydroxide. A most preferred base is sodium hydroxide. The pH adjustment is affected by dropwise addition of a saturated solution of sodium hydroxide in water to the reductant solution. A preferred reduction temperature is between 0 and 100 degrees Celsius. A most preferred reduction temperature is 37° C. A preferred reduction time is between 0.5 and 24 hours. A most preferred reduction time is 12 hours. A preferred liquid to solid ratio is from 5 to 100:1. A most preferred ratio is 20:1.

EXAMPLE 5

Production of Alpha and Gamma-Kerateine Fractions

Once the hair is reduced, the procedures for extracting and isolating the kerateines are identical as those described for the alpha- and gamma-keratoses. The only additional consideration is the relative solubility of kerateines. The relative solubility rankings in water is gamma-keratose>alpha-keratose>gamma-kerateine>alpha-kerateine from most to least soluble. That being the case, the production of resuscitation fluids from kerateines is facilitated by re-dissolving precipitated solutions in 20 mM tris base with 20 mM EDTA and dialyzing them. Typical dialysis conditions are 1 to 2% solution of kerateines dialyzed against deionized water for 24 to 72 hours. Those skilled in the art will recognize that other methods exist for the removal of low molecular weight contaminants in addition to dialysis (e.g. microfiltration, chromatography, and the like). The use of tris base is only required for initial solubilization of the kerateines. Once dissolved, the kerateines are stable in solution without the denaturing agent. Therefore, the denaturing agent can be removed without the resultant precipitation of kerateines. The final concentration of kerateines in these purified solutions can be adjusted by the addition/removal of water.

EXAMPLE 6

Formulation of Plasma Expander

Regardless of the form of the keratin, a final plasma expander composition is, in one embodiment, preferably formulated in Ringer's lactate. This electrolyte solution has the following formulation for 1,000 mL:
  3.1 g sodium lactate
  6.0 g sodium chloride
  300 mg potassium chloride
  200 mg calcium chloride The Ringer's lactate/keratin solution is formulated to match the desired viscosic and oncotic properties of blood. Suitable viscosities range from 1.0 to 5.0 centipoise. A most preferred viscosity is 2.5 centipoise. Suitable osmolarity ranges are from 100 to 500 mOsm/L. A most preferred osmolarity is approximately 300 mOsm. Alternatively, phosphate-buffered saline can also be used.

EXAMPLE 7

Preparation of Alpha-Keratose

Human hair was obtained from a local barber shop, cut in to pieces approximately ½ inch in length, washed with mild detergent and warm water, dried in air, washed with ethanol, and dried in air. 10 grams of this clean, degreased, dry hair was oxidized in 200 mL of 8 weight/volume (w/v) % of peracetic acid at 4° C. for 24 hours. The hair and oxidation solution was placed in a 2 L polyethylene jar and shaken on a reciprocating table shaker at 100 rpm. After oxidation, the liquid was removed by sieve and the hair rinsed with a copious amount of deionized (DI) water. The oxidized hair was extracted with 500 mL of a 0.3M sodium hydroxide solution at 4° C. for 24 hours. The extraction was performed in a 2 L polyethylene jar and shaken on a reciprocating table shaker at 100 rpm. After extraction, residual cuticle was removed by sieve and the liquid recovered. Small particulates were removed by centrifugation at 6,000 rpm for 30 minutes. The alpha-keratose was precipitated from the resulting liquid by dropwise addition of concentrated HCl to a pH of 4.2. The alpha-keratose was recovered by centrifugation at 2,000 rpm for 20 minutes and the remaining liquid ("supernatant") retained for future use. The alpha-keratose was re-dissolved in 20 mM tris base with 20 mM EDTA, re-precipitated by dropwise addition of HCl to a pH of 4.2. The alpha-keratose was recovered by centrifugation at 2,000 rpm for 20 minutes, re-dissolved in 20 mM tris base with 20 mM EDTA, and dialyzed against DI water using dialysis tubing with a low molecular weight cutoff (LMWCO) of 14,200.

EXAMPLE 8

Preparation of Gamma-Keratose

The supernatant from the extraction in Example 7 (i.e. pH 4.2 solution from the first precipitation of alpha-keratose) was concentrated 10-fold on a rotary evaporator using siphon vacuum and a water bath temperature of 50° C. The gamma-keratose was precipitated from this viscous solution by dropwise addition to an 8-fold excess of cold ethanol. The gamma-keratose was recovered by centrifugation at 2,000 rpm for 20 minutes, re-dissolved in a minimum volume of 20 mM tris base with 20 mM EDTA and residual alpha-keratose removed by acidification to pH 4.2 and removal of any precipitate that formed. The gamma-keratose was re-precipitated by dropwise addition of the remaining supernatant to an 8-fold excess of cold ethanol, and recovered by centrifugation at 2,000 rpm for 20 minutes. The gamma-keratose was dissolved in 20 mM tris base with 20 mM EDTA and dialyzed against DI water using dialysis tubing with a LMWCO of 3,500.

EXAMPLE 9

Preparation of Alpha-Kerateine

Human hair was obtained from a local barber shop, cut in to pieces approximately ½ inch in length, washed with mild detergent and warm water, dried in air, washed with ethanol, and dried in air. 10 grams of this clean, degreased, dry hair was reduced in 200 mL of 1M sodium thioglycolate at 4° C. for 24 hours. The sodium thioglycolate solution had been prepared by mixing thioglycolic acid with water, adjusting the pH to 10.2 by addition of a saturated solution of sodium hydroxide, and diluting to a final thioglycolic acid concentration of 1 mole per liter. The hair and reduction solution was placed in a 2 L polyethylene jar and shaken on a reciprocating table shaker at 100 rpm. After reduction, the liquid was removed by sieve and the hair rinsed with a copious amount of deionized (DI) water. The reduced hair was extracted with 500 mL of a 0.3M sodium hydroxide solution at 4° C. for 24 hours. The extraction was performed in a 2 L polyethylene jar and shaken on a reciprocating table shaker at 100 rpm. After extraction, residual cuticle was removed by sieve and the liquid recovered. Small particulates were removed by centrifugation at 6,000 rpm for 30 minutes. The alpha-kerateine was precipitated from the resulting liquid by dropwise addition of concentrated HCl to a pH of 4.2. The alpha-kerateine was recovered by centrifugation at 2,000 rpm for 20 minutes and the supernatant retained for future use. The alpha-kerateine was re-dissolved in 20 mM tris base with 20 mM EDTA, re-precipitated by dropwise addition of HCl to a pH of 4.2. The alpha-kerateine was recovered by centrifugation at 2,000 rpm for 20 minutes, re-dissolved in 20 mM tris base with 20 mM EDTA, and dialyzed against DI water using dialysis tubing with a low molecular weight cutoff (LMWCO) of 14,200.

EXAMPLE 10

Preparation of Gamma-Kerateine

The supernatant from the extraction in Example 9 (i.e. pH 4.2 solution from the first precipitation of alpha-kerateine) was concentrated 10-fold on a rotary evaporator using siphon vacuum and a water bath temperature of 50° C. The gamma-kerateine was precipitated from this viscous solution by dropwise addition to an 8-fold excess of cold ethanol. The gamma-kerateine was recovered by centrifugation at 2,000 rpm for 20 minutes, re-dissolved in a minimum volume of 20 mM tris base with 20 mM EDTA, and residual alpha-keratose removed by acidification to pH 4.2 and removal of any precipitate that formed. The gamma-keratose was re-precipitated by dropwise addition of the remaining supernatant to an 8-fold excess of cold ethanol, and recovered by centrifugation at 2,000 rpm for 20 minutes. The gamma-kerateine was dissolved in 20 mM tris base with 20 mM EDTA and dialyzed against DI water using dialysis tubing with a LMWCO of 3,500.

EXAMPLE 11

Preparation of Plasma Expanders

A solution of Ringer's lactate was prepared according to the following formula:
  3.1 g sodium lactate
  6.0 g sodium chloride
  300 mg potassium chloride
  200 mg calcium chloride
  Dilute to 1,000 mL with DI water
Solutions of alpha- and gamma-keratose, and alpha- and gamma-kerateine were prepared at concentrations of 0.5, 1.0, 2.0, 3.0, and 4.0 weight percent in Ringer's lactate. The osmolarity of each solution was measured on an Osmette A model 5002 osmometer (Precision Systems, Inc., Natick, Mass.). The data set forth in FIG. 1 was obtained.

EXAMPLE 12

Properties of Keratin Plasma Expanders

The keratin resuscitation fluids from example 11 were evaluated for thrombogenic potential by whole blood aggregometry. Fresh whole blood was drawn from healthy human volunteers and citrated by addition of 1 mL of 0.5 w/v % of trisodium citrate to 9 mL of whole blood. For each sample analysis, 750 µL of citrated blood was mixed 1:1 with Ringer's lactate solution and warmed to 37° C. in a cuvette placed in the test well of a Whole Blood Aggregometer, model 591 (Chrono-Log Corporation, Havertown, Pa.). The instrument was coupled to a PowerLab® 8sp analog to digital converter and computer running Chart 5 v5.1 data acquisition software (AD Instruments, Colorado Springs, Colo.). An impedance probe was placed in the cuvette and the resistance of the blood solution measured over time. After at least 2 minutes of steady baseline measurement, 100 µL of the test solution was injected into the blood solution. Any change in resistance was measured on the impedance probe. An increase in signal would be indicative of platelet aggregation and potential thrombogenicity. Keratin solutions were compared to a negative control, Ringer's lactate, and a positive control, 1 mg/mL collagen I solution. Data for the positive control and 2% alpha-keratose, gamma-keratose, and alpha-kerateine solutions are shown in FIG. 2.

EXAMPLE 13

Further Studies and Optimization

Figure 3:
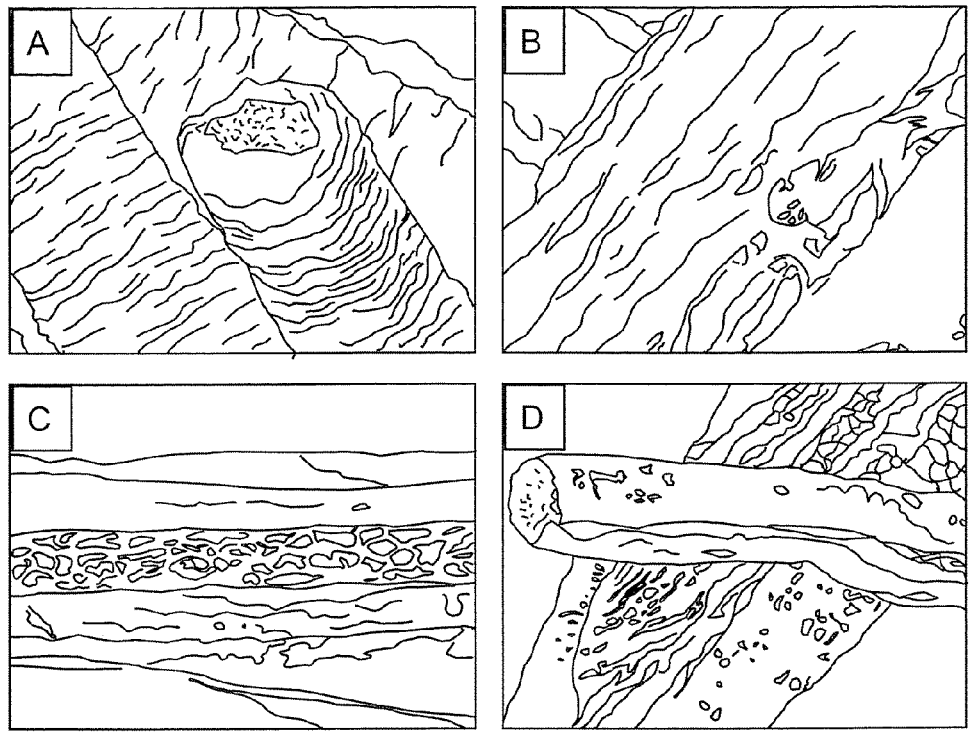
FIG. 3. (A, C) Oxidation or (B, D) reduction, followed by extraction in aqueous base removes essentially all the cortical proteins from hair fibers.

The extraction method development detailed in Examples 1 to 12 above focused on the production of keratoses and kerateines. The protocol for obtaining kerateines from hair fibers made use of a reductant that converts cystine crosslinks to cysteine residues. The initial reduction step, coupled with subsequent extractions with tris base, was highly effective at removing the cortical proteins from human hair fibers (FIG. 3). However, the thiol-functional cysteines are reactive and it was soon discovered that once the keratin is precipitated, some of the material will not readily re-dissolve. In fact, even in storage at −80° C., the kerateine samples, particularly the α-kerateines, would become completely insoluble even at basic pH. These samples became so intractable over time that it was not even possible to reduce them a second time in order to completely dissolve the proteins.

Figure 4:
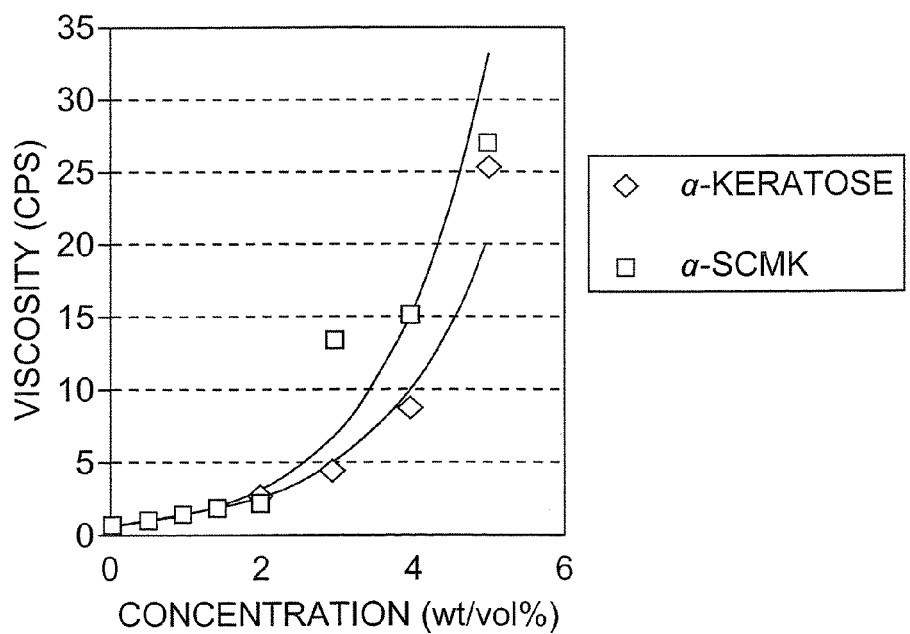
FIG. 4. Viscosity of keratin solutions at 37° C. Improved solubility and high viscosity was achieved with α-kerateine using a derivatization procedure that produced an scarboxymethyl analog. The α-keratose sample was obtained using a recently developed low-hydrolysis extraction method.

In an attempt to resolve this solubility problem, we utilized a derivatization procedure discussed by Crewther et al. (The Chemistry of Keratins. Anfinsen C B Jr., Anson M L, Edsall J T, and Richards F M, Editors. Advances in protein chemistry 1965. Academic Press. New York: 191-346). Briefly, once the kerateines had been extracted from the hair and before precipitation of the alpha fraction, an s-carboxymethyl group can be grafted onto the cysteine residue by reaction with iodoacetic acid. This was accomplished by dialyzing the crude extract solution to remove residual reductant, then adding an excess of iodoacetic acid to the protein solution. After reaction for several hours, the alpha and gamma s-carboxymethylkerateines (SCMK) could be separated as usual. This method was successful in producing α-SCMK that was soluble at neutral pH, and of relatively high viscosity (FIG. 4). However, upon testing with whole blood, the sample was determined to instigate excessive RBC aggregation. Although no further testing of the α-SCMK was conducted after it was determined that RBCs aggregate in the presence of this material, recent developments discussed later in this section suggest that α-SCMK can be further purified to remove the causative material.

Figure 5A:
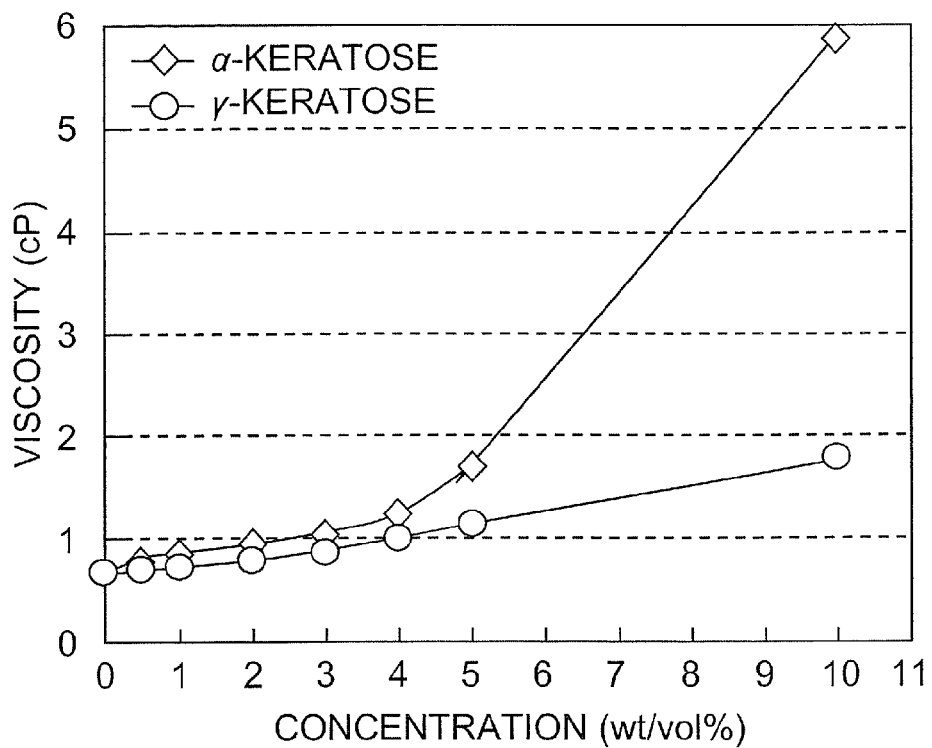
FIG. 5. Viscosity (a) and osmolarity (b) curves for keratose fluids formulated in Ringer's lactate solution and adjusted to pH 7.4. The target viscosity for a hyperviscous fluid is approximately 8 cP (whole blood is ca. 4, depending on location in the body). The osmolarity of whole blood is approximately 300 mOsm/kg. These data were obtained using an early extraction protocol that resulted in excessive hydrolysis, as suggested by the relatively low viscosity achieved at concentrations as high as 10 weight %.
Figure 5B:
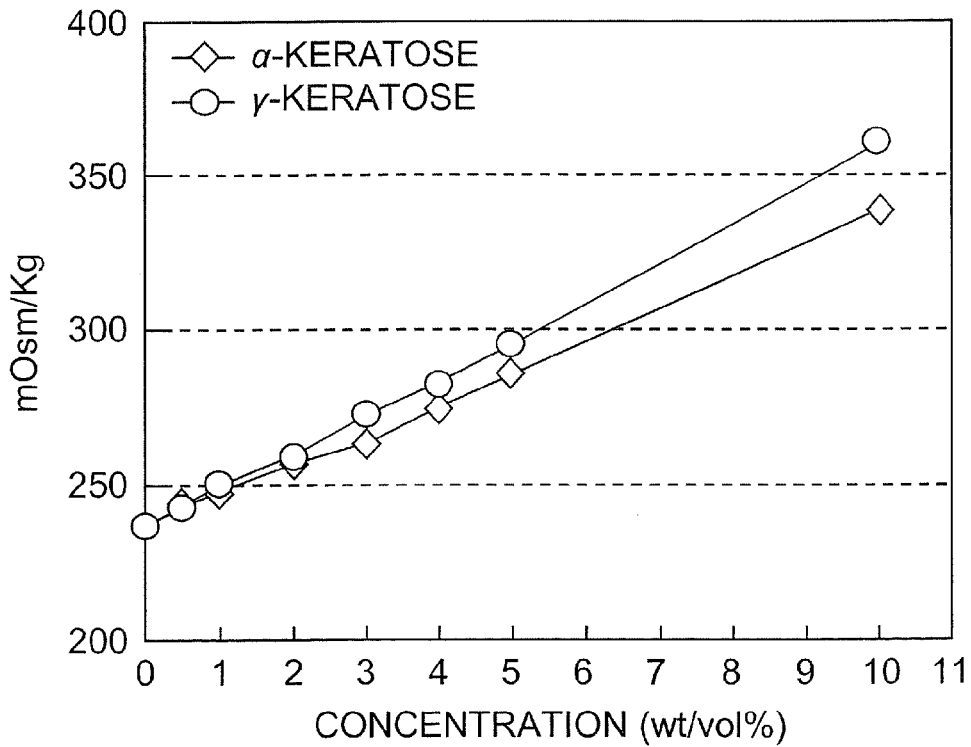

In contrast to the kerateine materials, and as expected, keratose samples demonstrated no apparent solubility problems. This is due to the conversion of cystine to non-reactive and hydrophilic sulfonic acid residues during the oxidative reaction rather than the highly reactive cysteine residues created during the reduction protocol. Preparation of viscous solutions was relatively simple and fluids formulated in Ringer's lactate were prepared and tested for viscosity and osmolarity (FIG. 5). The resulting viscosity of the α-keratose sample was unacceptably low, even at a relatively high concentration of 10 weight percent. The viscosity of the γ-keratose was also too low to be considered effective in the FCD model of resuscitation, but this was expected since the difference in molecular weight between alpha and gamma is nearly 5-fold. The osmolarity obtained from these samples was within acceptable limits (FIG. 5b)

Figure 6A:
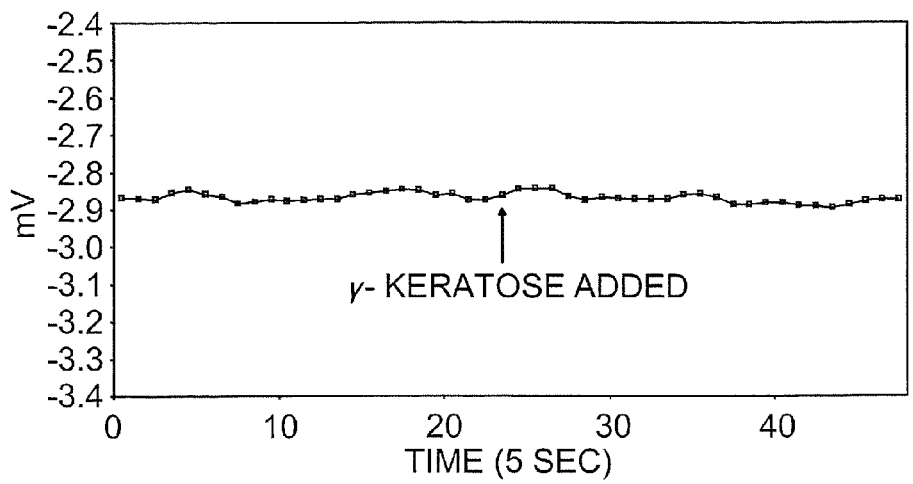
FIG. 6. Impedance measurement of lightly citrated human whole blood with the addition of 100 μL of γ-keratose (a), α-keratose (b), and collagen 1 (c; +control). Lack of a detectable baseline shift suggests non-thrombogenic properties and good blood compatibility.
Figure 6B:
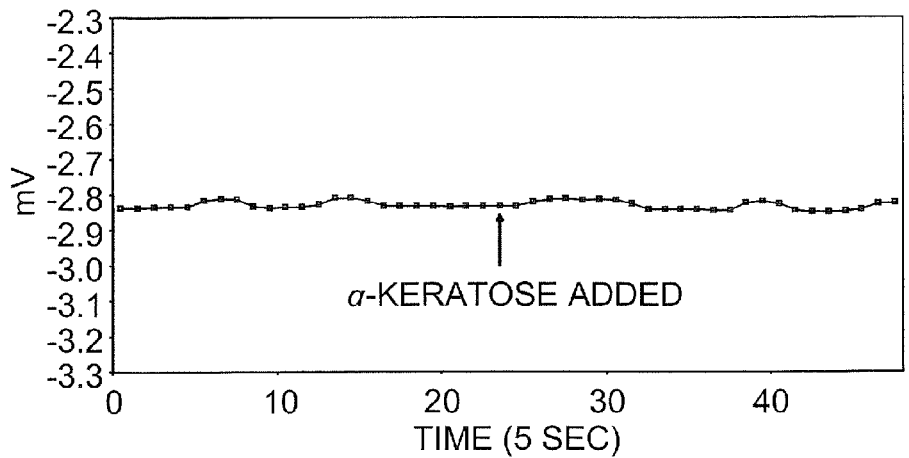
Figure 6C:
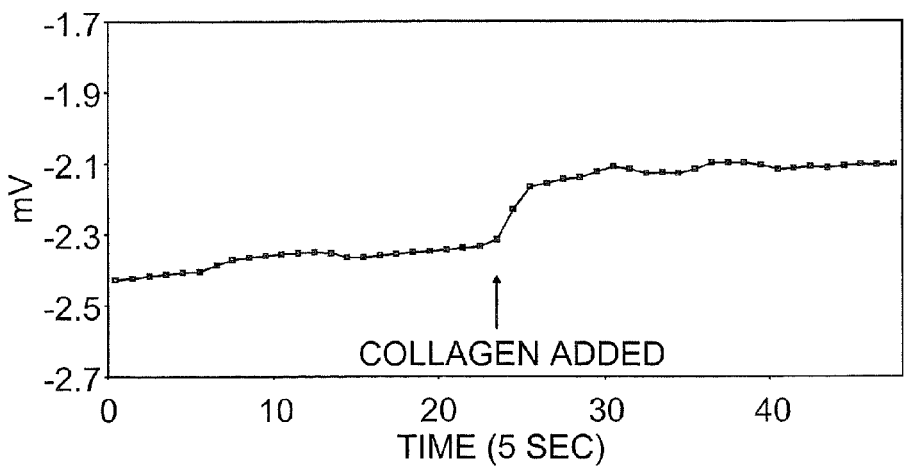

RBC aggregation studies of these two fluids were conducted using a whole blood aggregometer. A technique was developed wherein human blood was lightly citrated so as to provide reasonable working time without interfering with platelet function. Results of these experiments for the keratose solutions at 4 weight percent and a positive control, collagen 1, are shown in FIG. 6. This technique measures a change in impedance as RBC and platelets aggregate on a microprobe immersed in a 1:1 mixture of blood and DI water. After baseline equilibration, a small amount of the test solution is added and the change in impedance across the sensor is monitored. As can be seen in FIG. 6, there is essentially no resulting baseline deflection when the keratose fluids are added, suggesting that the RBC are not aggregated and the platelets similarly are not activated by this material. In contrast, collagen 1, a known thrombogenic protein, elicits an immediate baseline shift. Further evidence of blood compatibility was obtained from microscopic examination of these mixtures. Light micrographs show no visible evidence of RBC aggregation or platelet activation in slightly citrated samples (FIG. 7).

To further demonstrate the biocompatibility and safety of these keratose fluids, a 4 weight percent solution of α-keratose in Ringer's lactate was prepared and sterile filtered. This solution was used in a top load study in mice. The objective of these experiments was simply to assess the safety of our fluid formulation in a conservative model. A small bolus representing 10% of the total blood volume of the mouse was used to assess the systemic effects of a small amount of keratin biomaterial in the circulation. All animals recovered without incident. Chemistry and CBC analysis showed that the animals had recovered a normal blood profile within the 24 hour period (Tables 1 and 2, respectively).

TABLE 1

Blood chemistry results for samples taken from mice subjected to a 10% top load IC injection (Control = no injection; RL = Ringer's lactate; keratin = 4 w/v % α-kertose)

|  | Glucose (mg/dL) | ALT (U/L) | Alb (g/dL) | Alk P (U/L) | AST (U/L) | Bili-T (mg/dL) | BUN (mg/dL) | $Ca^{2+}$ (mg/dL) | Creat (mg/dL) | Phos (mg/dL) | TP (g/dL) |
|---|---|---|---|---|---|---|---|---|---|---|---|
| Day 1 | | | | | | | | | | | |
| Control | 157 | 41 | 2.8 | 17 | 54 | 0.8 | 20 | 9.9 | 0.30 | 6.2 | 4.7 |
| RL | 228 | 47 | 2.9 | 5 | 80 | 1.5 | 17 | 9.9 | 0.27 | 7.4 | 5.3 |
| Keratin | 155 | 38 | 2.6 | 7 | 44 | 0.7 | 20 | 9.7 | 0.17 | 7.2 | 4.9 |
| Day 5 | | | | | | | | | | | |
| Control | 270 | 32 | 2.9 | 9 | 54 | 0.9 | 18 | 7.2 | 0.22 | 6.3 | 5.3 |
| RL | 203 | 26 | 2.6 | 31 | 71 | 0.6 | 19 | 7.3 | 0.25 | 6.9 | 4.6 |
| Keratin | 214 | 21 | 2.8 | 6 | 53 | 0.5 | 22 | 7.3 | 0.18 | 6.0 | 5.0 |

TABLE 2

Electrolytes and CBC from blood taken from mice subjected to a 10% top load IC injection (Control = no injection; RL = Ringer's lactate; keratin = 4 w/v % α-kertose)

|  | PCV (%) | Hgb (g/dL) | MCV (fl) | WBC (×1000) | RBC (×1000) | NA* (mmol/L) | $K^+$ (mmol/L) | $Cl^-$ (mmol/L) |
|---|---|---|---|---|---|---|---|---|
| Day 1 | | | | | | | | |
| Control | 28 | 13 | 46.6 | 41 | 6.01 | 144 | 5.2 | 111 |
| RL | 32 | 14.4 | 47.4 | 54 | 6.69 | 146 | 5.4 | 110 |
| Keratin | 27 | 12.3 | 49 | 23 | 5.59 | 147 | 5.5 | 111 |
| Day 5 | | | | | | | | |
| Control | 41 | 16.6 | 51.4 | 15.2 | 7.97 | 142 | 8.7 | 106 |
| RL | 43 | 16.9 | 49.7 | 5.5 | 8.74 | 143 | 7.4 | 111 |
| Keratin | 35 | 16 | 47.7 | 1.9* | 7.32 | 144 | 8.1 | 113 |

*Sample viscosity was to high to produce consistent results

It was apparent from these data that although RBC aggregation properties and cardiovascular compatibility were favorable, viscosity of these samples was too low to be effective in the FCD model. In hindsight, it was probably due in part to the excessive hydrolysis, particularly of the α-keratose, that the fluids did not instigate RBC aggregation and were highly compatible in the circulation. Sodium dodecyl-sulfate-poly(acrylamide) gel electrophoresis (SDSPAGE) analysis of these samples confirmed that hydrolysis was prevalent (data not shown). A new extraction protocol was developed wherein the initial oxidation step was unchanged, but the tris base concentration in the initial extraction step was halved. In addition, second and third extraction steps were added using DI water that served not only to dilute residual tris base, but also increased the yield of protein (see Example 1 above).

Viscosity of the α-keratose fraction isolated using this method was well within acceptable limits (FIG. 4). However, a fluid formulation in PBS still demonstrated excessive RBC aggregation characteristics. To address this, a simple ion exchange purification step was devised. A sample of low-hydrolysis α-keratose was produced and dissolved at ca. 2 weight % in 100 mM tris base and the pH adjusted to 8.5 by addition of HCl. It is well published in the literature that hair keratin proteins exist as acidic and basic families. The terms "acidic" and "basic" are descriptors commonly used in the literature to describe sub-families of keratins that have different isoelectric points. Both sub-classes are soluble at neutral pH and can be effectively separated chromatographically. Ion exchange chromatography is a convenient, inexpensive, and scalable method for separating such mixtures.

Samples of acidic and basic α-keratose were generated using a flash chromatography column containing a commercially available resin. The fractions were dialyzed against DI water, concentrated, and freeze dried. Resuscitation fluid formulations using these fractions were prepared at 5 weight percent concentration and their RBC aggregation characteristics evaluated with fresh whole human blood. As is shown in FIG. 8, the ion exchange chromatography was highly effective and separating the aggregation phenomenon. Basic α-keratose was essentially free from interactions with blood cells while the acidic α-keratose caused excessive aggregation.

Figure 9:
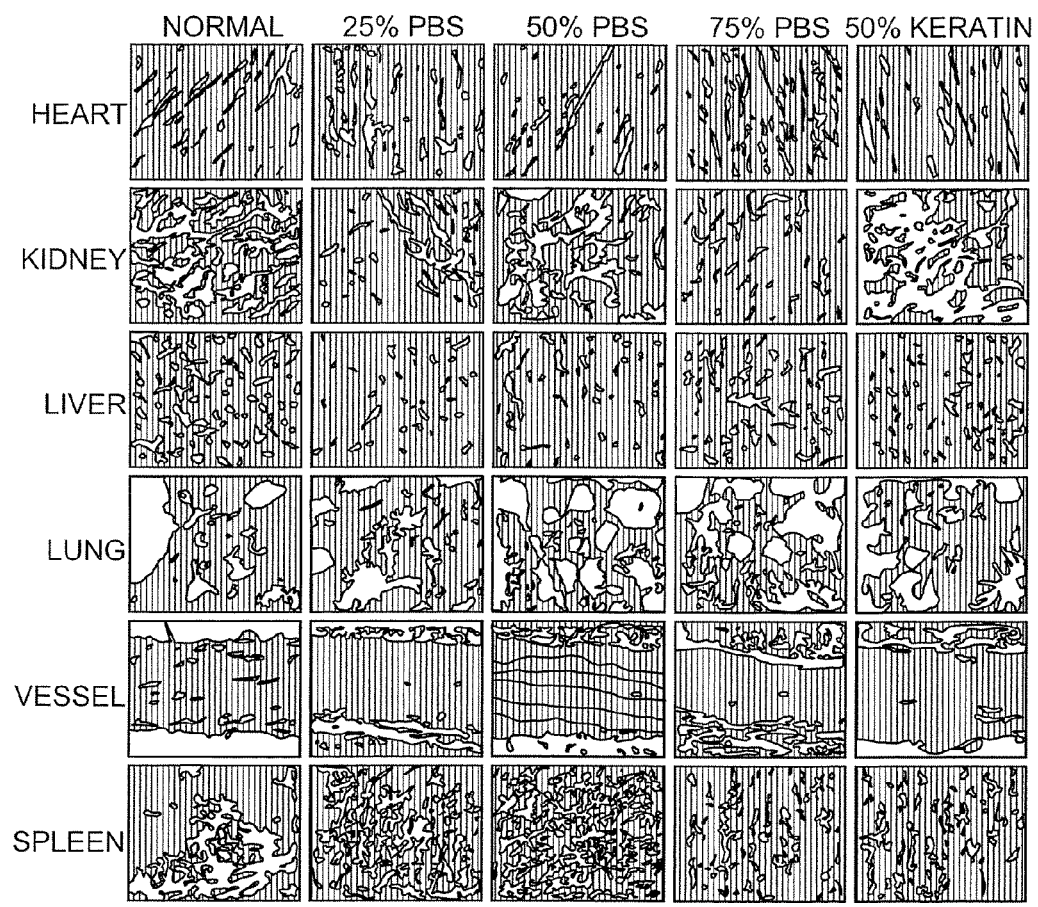
FIG. 9. Histology of major organs harvested from rats subjected to simultaneous fluid exchange. All animals recovered from the surgeries without incident and no deleterious effects were noted in any of the tissues. (Magnification ×200)

Based on these results confirming the isolation of a viscous, blood compatible keratin biomaterial, a resuscitation fluid formulation was tested in a simultaneous fluid exchange model. Again, the goal of this experiment was to assess the safety of the keratin fluid, albeit in a more aggressive model than previously described. Relatively large male rats were catheterized so that fluid could be simultaneous exchanged using two synchronized syringe pumps. Large volumes of blood were exchanged with PBS (control) and basic α-keratose fluid as a means to test the interaction of the keratin biomaterial in a dynamic circulatory system. All of the rats recovered from the procedure without incident (Table 3) and were sacrificed after 24 hours. Histology on the vital organs showed no deleterious effects with PBS or keratin (FIG. 9).

TABLE 3

Results of CBC and blood chemistry from samples taken 24 hours after simultaneous fluid exchange in male Fisher rats

| Test | PBS 25% | PBS 50% | PBS 75% | Keratin 50% |
|---|---|---|---|---|
| PCV (%) | 24.4 | 18.7 | 15.7 | 20.2 |
| Hgb (g/dl) | 9.6 | 8.3 | 7.1 | 8.9 |
| MCV (fl) | 54 | 53.3 | 54 | 54.2 |
| WBC (×1000) | 4.7 | 9.6 | 10 | 12.8 |
| RBC (×1000) | 4.52 | 3.51 | 2.91 | 3.73 |
| Glucose (mg/dl) | 157 | 141 | 109 | 96 |
| ALT (U/l) | 76 | 76 | 143 | 148 |
| Alb (g/dl) | 3.6 | 3.1 | 3.1 | 1.6 |
| Alk P (U/l) | 87 | 130 | 121 | 131 |
| AST (U/l) | 378 | 152 | 339 | 472 |
| Bili-T (mg/dl) | 0.5 | 0.6 | 0.9 | 0.9 |
| BUN (mg/dl) | 14 | 10 | 14 | 14 |
| Ca 2+ (mg/dl) | 7.7 | 8.4 | 8.5 | 8.2 |
| Creat (mg/dl) | 0.51 | 0.48 | 0.42 | 0.59 |
| Phos (mg/dl) | 8 | 7.9 | 8.2 | 7.1 |
| TP (g/dl) | 6.1 | 5.9 | 5.6 | 6.1 |

Materials and Methods

Animal testing was performed under an approved protocol. Regulations of the Wake Forest University Health Sciences Animal Care and Use Committee were followed at all times.

Keratose Fractions. Keratose fractions were obtained using the method of Alexander and coworkers (Alexander P, Hudson R F, and Fox M. The reaction of oxidizing agents with wool: The division of cysteine into two fractions of widely differing reactivities. *Biochem J* 1950; 46:27-32) and processed as described in Example 1 above.

Viscosity Measurements. Sample solutions were prepared at keratin concentrations ranging from 1 to 10 weight percent. The viscosity of each solution was tested dynamically on a Viscometer (Model DV-I+, Brookfield Engineering Laboratories Inc.), using a cone and plate geometry with a cone angle of 0.02 radians. The samples were maintained at 37° C. using a constant frequency of 30 rotations per minute. The following analysis procedure was followed: 1) stabilize the test geometry at 37° C.; 2) open the heated chamber and load sample; and 3) close the chamber and allow ca. 2 minutes for the temperature to reach 37° C. before the measurement was initiated.

Osmolality Measurements Osmometry was conducted on an Osmette A model 5002 osmometer (Precision Systems, Inc., Natick, Mass.). Solutions at keratin concentrations of 0.5, 1.0, 2.0, 3.0, and 4.0 weight percent were evaluated by adding 2 mL in a cuvette and measuring freezing point depression.

Whole Blood Aggregation Measurements. Aggregometry experiments were performed using a Whole Blood Aggregometer, model 591 (Chrono-Log Corporation, Havertown, Pa.), coupled to a PowerLab®, 8sp analog to digital converter and PC running Chart 5 v5.1 data acquisition software (AD Instruments, Colorado Springs, Colo.). Additionally, 1:1 mixtures of 4 wt. % keratin solutions with whole blood were observed by optical microscopy for evidence of RBC aggregation.

Mouse Top Load Study. CD-1 outbred mice were anesthetized with 3% isoflurane and immobilized on a procedure table. The heart was located visually and by palpation and a small 27.5 gauge needle inserted into the heart; a small amount of blood was withdrawn to ensure the location of the needle. A bolus of 4 weight % keratin that represented and estimated 10% of the total blood volume of the mouse was slowly injected. Ringer's lactate was used as a control. After the needle was withdrawn, the animal was allowed to recover. After 24 hours and again after 5 days, ca. 1 mL of blood was drawn using a similar procedure for CBC and chemistry.

Ion Exchange Chromatography. Samples were loaded on to a 200 mL flash chromatography column containing DEAE Sepharose™ weak anionic ion exchange resin in 10 mM tris base at pH 6. Basic α-keratose was eluted from the column with 100 mM tris base plus 2M NaCl at pH 12. The eluate was neutralized and dialyzed against DI water using an ultrafiltration tangential flow cartridge with a nominal low molecular weight cutoff of 5 KDa, concentrated by rotary evaporation, and freeze dried.

Rat Fluid Exchange Study Under general anesthesia, subcutaneous incisions were made in the neck and thigh of male Fisher rats weighing 300 to 350 grams. Angiocatheters connected to two syringe pumps were inserted into the lumen of the femoral and jugular veins so that simultaneous infusion and withdraw could be performed. The syringe pumps were synchronized to deliver and withdraw at the same rate (ca. 1.0 mL/min). The fluid exchange transpired over approximately 15 to 20 minutes, depending on animal weight, during which the animal's vital signs were monitored. Fluids included a phosphate buffered saline control and basic α-keratose. After fluid exchange, the catheters were removed and hemostasis confirmed prior to wound closure in 2 layers with absorbable sutures. Approximately 24 hours after recovery, the animals were sacrificed and blood and vital organs harvested for analysis.

Blood Chemistry. Arterial $pO_2$, $pCO_2$ and pH at 37° C. using a pH/blood gas analyzer (Chiron Diagnostics, Model 248) were measured from arterial blood sampled from the carotid artery into heparizined capillary tubes. Hemoglobin content of blood was determined from a drop of blood using a handheld photometer device (B-Hemoglobin Photometer Hemocue, Angelholm, Sweden). Whole blood lactate was measured from a 25 µL sample using a YSI Sport Lactate Analyzer.

Tissue Histology. Vital organs were removed and flash frozen in liquid nitrogen. The tissues were microtomed, fixed, and stained with hematoxylin and eosin (H&E).

The foregoing is illustrative of the present invention, and is not to be construed as limiting thereof. The invention is defined by the following claims, with equivalents of the claims to be included therein.

That which is claimed is:

1. A method of increasing plasma volume in a subject in need thereof, comprising administering said subject a liquid plasma expander in an amount effective to increase the plasma volume of said subject, wherein said plasma expander consists essentially of:
   (a) from 0.1 to 10 percent by weight of basic alpha keratose; said basic alpha keratose produced by the process of separating basic alpha keratose from a mixture of acidic and basic alpha keratose by ion exchange chromatography; and with said basic alpha keratose having an average molecular weight of from 10 to 100 kilodaltons;
   (b) from 0 to 5 percent by weight of gamma keratose; and
   (c) from 90 to 99.9 percent by weight of an electrolyte solution; with said basic alpha keratose and said gamma keratose solubilized in said electrolyte solution to form a homogeneous liquid composition having:
      (i) a pH of 7-8;
      (ii) an osmolarity of 200 to 500 milliosmoles/Liter; and
      (iii) a viscosity of 2 to 20 centipoise at a temperature of 37 degrees Celsius as determined with a Brookfield viscometer having a cone and plate geometry with a cone angle of 0.02 radians at a constant frequency of 30 rotations per minute.

2. The method of claim 1, wherein said subject is a trauma or burn victim.

3. The method of claim 1, wherein said composition has a viscosity of 4 to 20 centipoise at a temperature of 37 degrees Celsius using a cone and plate geometry with a cone angle of 0.02 radians and a constant frequency of 30 rotations per minute.

4. The method of claim 1, wherein said composition has a viscosity of 10 to 20 centipoise at a temperature of 37 degrees Celsius using a cone and plate geometry with a cone angle of 0.02 radians and a constant frequency of 30 rotations per minute.

5. The method of claim 1, wherein said composition has a viscosity of 10 to 15 centipoise at a temperature of 37 degrees Celsius using a cone and plate geometry with a cone angle of 0.02 radians and a constant frequency of 30 rotations per minute.

6. The method of claim 1, wherein said plasma expander consists essentially of:
   (a) from 0.1 to 5 percent by weight of said basic alpha keratose;
   (b) from 0 to 5 percent by weight of gamma keratose; and
   (c) from 90 to 99.9 percent by weight of an electrolyte solution.

7. The method of claim 1, wherein said plasma expander consists essentially of:
   (a) from 0.1 to 4 percent by weight of said basic alpha keratose;
   (b) from 0 to 4 percent by weight of gamma keratose; and
   (c) from 92 to 99.9 percent by weight of an electrolyte solution.

8. The method of claim 1, wherein when said plasma expander is contacted to red blood cells forms aggregates of said blood cells of less than 25 microns in diameter.

9. The method of claim 1, wherein said process further comprises the steps of precipitating said basic alpha keratose; re-dissolving said basic alpha keratose in a denaturing solution, optionally in the presence of a chelating agent to complex trace metals; and re-precipitating said basic alpha keratose from said denaturing solution.

10. The method of claim 9, wherein said denaturing solution comprises a buffer solution.

11. The method of claim 9, wherein said denaturing solution comprises a TRIS buffer solution.

12. The method of claim 1 further comprising administering to said subject red blood cells (RBCs).

13. The method of claim 12, wherein said red blood cells are mammalian.

14. The method of claim 12, wherein said red blood cells are human.

* * * * *

UNITED STATES PATENT AND TRADEMARK OFFICE
CERTIFICATE OF CORRECTION

PATENT NO. : 8,021,830 B2  
APPLICATION NO. : 12/209773  
DATED : September 20, 2011  
INVENTOR(S) : Van Dyke Page 1 of 1

It is certified that error appears in the above-identified patent and that said Letters Patent is hereby corrected as shown below:

In the Patent:

Column 2, Line 48: Please correct "434, 54-61 (1977))"
to read -- 434, 354-61 (1977)) --

Column 11, Line 62: Please correct "with 25000 mL" to read -- with 2,000 mL --

Column 12, Line 1: Please correct "as DEAL" to read -- as DEAE --

Signed and Sealed this
Third Day of January, 2012

David J. Kappos
*Director of the United States Patent and Trademark Office*